United States Patent [19]

Yoshimura et al.

[11] Patent Number: 5,057,605

[45] Date of Patent: * Oct. 15, 1991

[54] SIALOCYLGLYCEROLIPIDS AND METHOD FOR PREPARING THE SAME

[75] Inventors: Shoji Yoshimura, Iruma; Yuzi Matsuzaki, Tokorozawa; Mamoru Sugimoto, Tokyo; Masayoshi Ito, Kunitachi; Yoshiyasu Shitori, Tokyo; Tomoya Ogawa, Musashino, all of Japan

[73] Assignee: Mect Corporation, Tokyo, Japan

[*] Notice: The portion of the term of this patent subsequent to Jan. 10, 2006 has been disclaimed.

[21] Appl. No.: 269,697

[22] Filed: Nov. 10, 1988

[30] Foreign Application Priority Data

Nov. 10, 1987 [JP] Japan .................. 62-283491

[51] Int. Cl.$^5$ ............... C07H 1/00; C07H 11/00; C07H 15/00
[52] U.S. Cl. .................. 536/4.1; 536/17.2; 536/17.9; 536/18.2; 536/18.6; 536/115; 536/120; 536/121; 536/124
[58] Field of Search ............ 536/4.1, 18.2, 17.2, 536/18.6, 17.9, 115, 120, 124, 121

[56] References Cited

U.S. PATENT DOCUMENTS 4,797,477  1/1989  Yoshimura et al. ............... 536/17.2

Primary Examiner—Ronald W. Griffin
Assistant Examiner—Everett White
Attorney, Agent, or Firm—Oblon, Spivak, McClelland, Maier & Neustadt

[57] ABSTRACT

Sialocylglycerolipids represented by the following general formula (I):

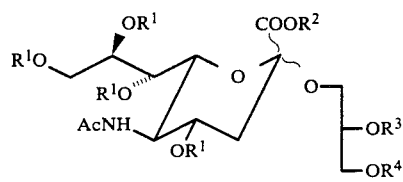

wherein $R^1$ represents a hydrogen atom or a group $CH_3CO$—; $R^2$ represents an alkali metal, a hydrogen atom or a lower alkyl group; $R^3$ represents a hydrogen atom or a group $C_nH_{2n+1}$— (n is an integer ranging from 1 to 30); and $R^4$ represents a group $C_mH_{2n+1}$— (m is an integer ranging from 1 to 30) are herein disclosed. They are prepared by treating a corresponding compound in an alkaline aqueous solvent. The method makes it possible to provide these compounds in a high yield by a simple processes.

13 Claims, No Drawings

SIALOCYLGLYCEROLIPIDS AND METHOD FOR PREPARING THE SAME

BACKGROUND OF THE INVENTION

1. Field of the Invention

The present invention relates to novel sialocylglycerolipids as alkali metal salts of sialic acid-containing lipid derivatives and a method for preparing the same.

2. Description of the Prior Art

In general, most of the diseases resulting from neuropathy are considered to be difficult to treat or cure. In addition, a rather small number of therapeutic agents therefore have been developed.

Examples thereof which are clinically tried at present are naturally occurring gangliosides (sold under the trade name of Cronassial; see Japanese Patent Un-examined Publication (hereunder referred to as "J.P. KOKAI") No. 52-34912) and mecobalamin (general name of medicine) which is a vitamins. However, they do not have a satisfactory effect on these diseases and, therefore, there is a demand for the development of further improved therapeutic agents.

In addition, acidic glycolipids such as ganglioside and such acidic phospholipids such as phosphatidyl inositol and phosphatidyl serine are known which play an important roles in neurotransmitting systems of animals. The inventors of this invention have found that a mixture of gangliosides or a single component present in a ganglioside promotes the proliferation of primarily cultured nerve cells and neuroblastoma cells and promotes the formation of neurites and the extensions thereof. Further, they exhibit an effect similar to that of mecobalamin in animal models and one of the inventors already filed a patent application (see J.P. KOKAI No. 59-222424).

As already discussed above, the ganglioside mixtures are, for the present, used in the treatment of peripheral nerve disorders or central nerve disorders. However, since these gangliosides are natural products extracted from different animals, a problem of antigenicity due to the gangliosides per se or impurities arises.

Besides, it is very difficult to establish a strict standard therefore since they are not necessarily pharmaceutically stable and uniform.

On the other hand, sialic acid present in these gangliosides is also found in, for instance, glycoproteins or exists in cell surfaces of animals or bacteria. Recently, they are attracting much attention from the medical and pharmacologic viewpoint as materials involved in immunity, cancer, inflammation, various infections, cell differentiation, hormone receptors and the like. There is no report on the therapeutic effects of sialic acid-containing lipid derivatives on nerve disorders.

Taking this fact into consideration, the inventors of the present invention found that a sialocylglycerolipid, which is a sodium salt of a derivative of a sialic acid-containing lipid, i.e., (3-0-(sodium-(5-acetamido-3,5-dideoxy-alpha-D-glycero-D-galacto-2-nonulopyranosyl) -onato)-1,2-di-0-tetradecyl-Sn-glycerol) shows a neurite extention effect and that it might suitably be used in improving or treating nerve diseases (see Japanese Patent Application Serial (hereunder referred to as "J.P.A.") No. 61-214787).

It would be expected that other sialocylglycerolipids likewise might show an effect similar to the aforementioned offset, but the synthesis of such a lipid has not yet been reported.

Japanese Patent Publication for Opposition Purpose (hereunder referred to as "J.P. KOKOKU") No. 59-164798 discloses that a variety of derivatives of sialic acid can be obtained by converting sialic acid to a sugar donor according in a known method and then reacting it with a sugar acceptor which is likewise obtained in a known manner.

However, this method proceeds in accordance with the following processes and thus improvements must be made on many points.

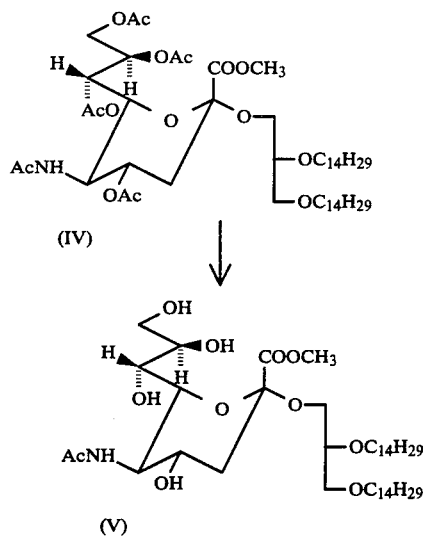

wherein Ac represents an acetyl group.

More specifically, the above mentioned method comprises dissolving Compound (IV) in methanol, adding 1N NaOCH$_3$ thereto, stirring the solution at room temperature for one hour, then neutralizing the solution with Amberlist A-15 (trade mark) followed by filtering the same, concentrating it under a reduced pressure to precipitate Compound (V) in a yield of 67%. However, in this method, the yield of the desired product is very low and the product must further undergo the following three steps to provide compound (VI) which is effective for treating nervous diseases.

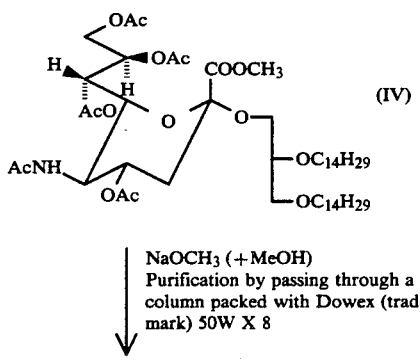

-continued

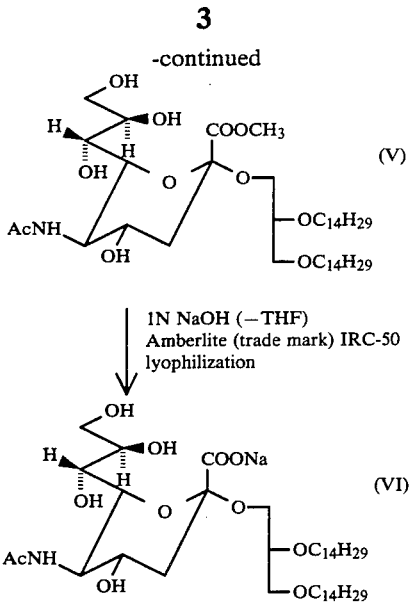

In order to solve these problems accompanied by the conventional method, the inventors of the present invention developed the following method and filed a patent application relating to such a method (J.P.A. No. 61-189340). This method comprises hydrolyzing a compound represented by the following general formula (VII):

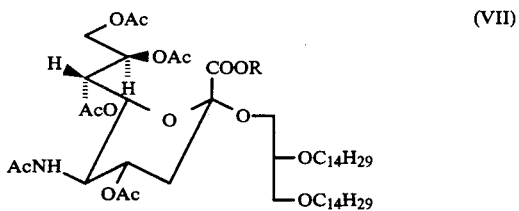

wherein Ac is the same as defined above and R represents a lower alkyl group, in a solution of sodium hydroxide in ROH or an aqueous solution of tetrahydrofuran (THF) and then separating and purifying the product by reverse phase column chromatography to recover a compound represented by the following general formula (VI):

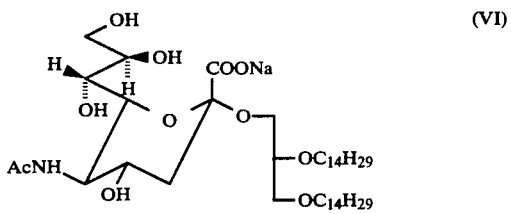

wherein Ac is the same as defined above.

However, at the time of filing the aforementioned patent application, the kind of molecules to which this method for preparing sialocylglycerolipids having high biological activity can be applied (see J.P.A. No. 61-214787) was still unclear and solvents which could be used in the reaction were not specified.

SUMMARY OF THE INVENTION

It is a primary object of the present invention to provide novel sialocylglycerolipids which are sodium salts of sialic acid-containing lipid derivatives.

Another object of the present invention is to provide a method for preparing such sialocylglycerolipids.

Consequently, according to an aspect of the present invention, sialocylglycerolipids represented by the following general formula (I):

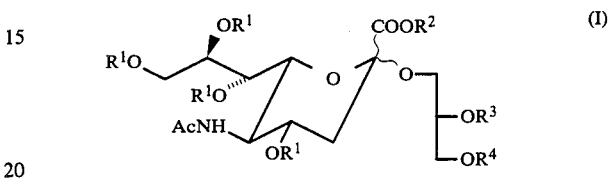

wherein $R^1$ represents a hydrogen atom or a group $CH_3CO-$, $R^2$ represents an alkali metal, a hydrogen atom or a lower alkyl group, $R^3$ represents a hydrogen atom or a group $C_nH_{2n+1}-$ (n is an integer ranging from 1 to 30) and $R^4$ represents a group $C_mH_{2m+1}-$, m is an integer ranging from 1 to 30, are provided.

DETAILED EXPLANATION OF THE INVENTION

Preferred examples of the sialocylglycerolipids of the present invention include those represented by the general formula (I) in which $R^2$ is a sodium atom, $R^3$ is a group $C_nH_{2n+1}$ (n is 6, 10, 18 or 22) and $R^4$ is a group $C_mH_{2m+1}$ (m is 6, 10, 18 or 22).

The compounds of the present invention can be prepared according to the methods disclosed in J.P.A. Nos. 61-189340 and 61-214787 filed by the same applicant, i.e., the assignee of this invention or the method of the present invention which will be detailed below.

More specifically, Compound (1) in which Bn represents a benzyl group is reacted with 1-bromoalkane to form Compound (2). Then, Compound (2) is subjected to debenzylation to obtain Compound (3) (see Agric. Biol. Chem., 1982, Vol. 46(1), p. 255; and Biochemistry, 1963, Vol. 2, p. 394).

On the other hand, Compound (4) (wherein Ac is the same as defined above) can be obtained from sialic acid (N-acetylneuraminic acid) according to Kuhn's method (see Chem. Ber., 1966, Vol. 99, p. 611).

Compound (4) thus obtained is reacted with Compound (3) obtained above to form Compound (5) (alpha-form) and Compound (6) (beta-form) followed by separating Compound (5), deacetylating and hydrolyzing it to form Compound (7) of the present invention. In this respect, the hydrolysis may be performed in THF or an alcohol such as methanol or ethanol. Preferably, it is performed in such a solvent under an alkaline conditions. In addition, if the synthesis is carried out using other halogenoalkanes such as bromoalkanes, Compounds (13), (19), (25) or the like can be prepared.

The details of these reactions are as follows:

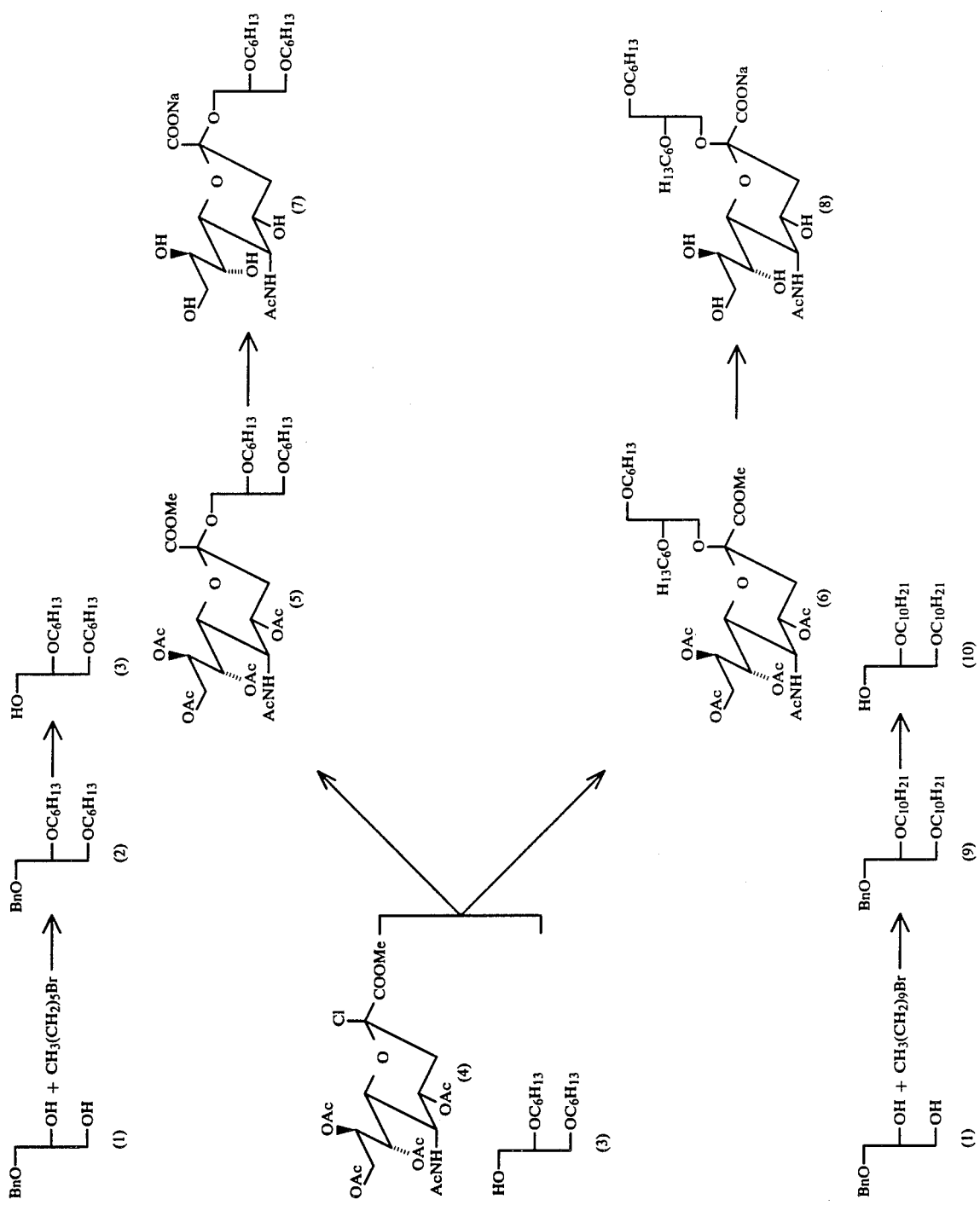

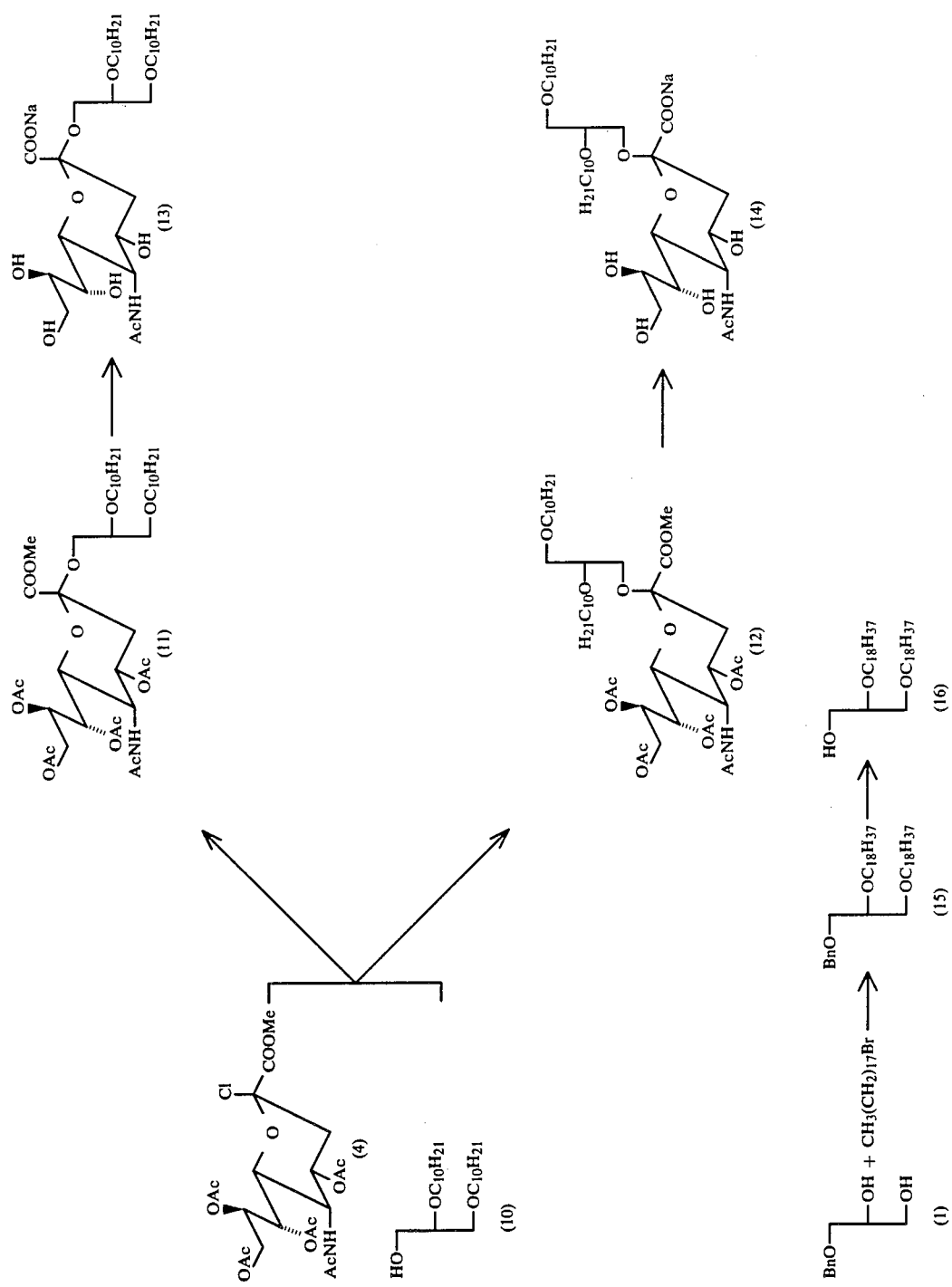

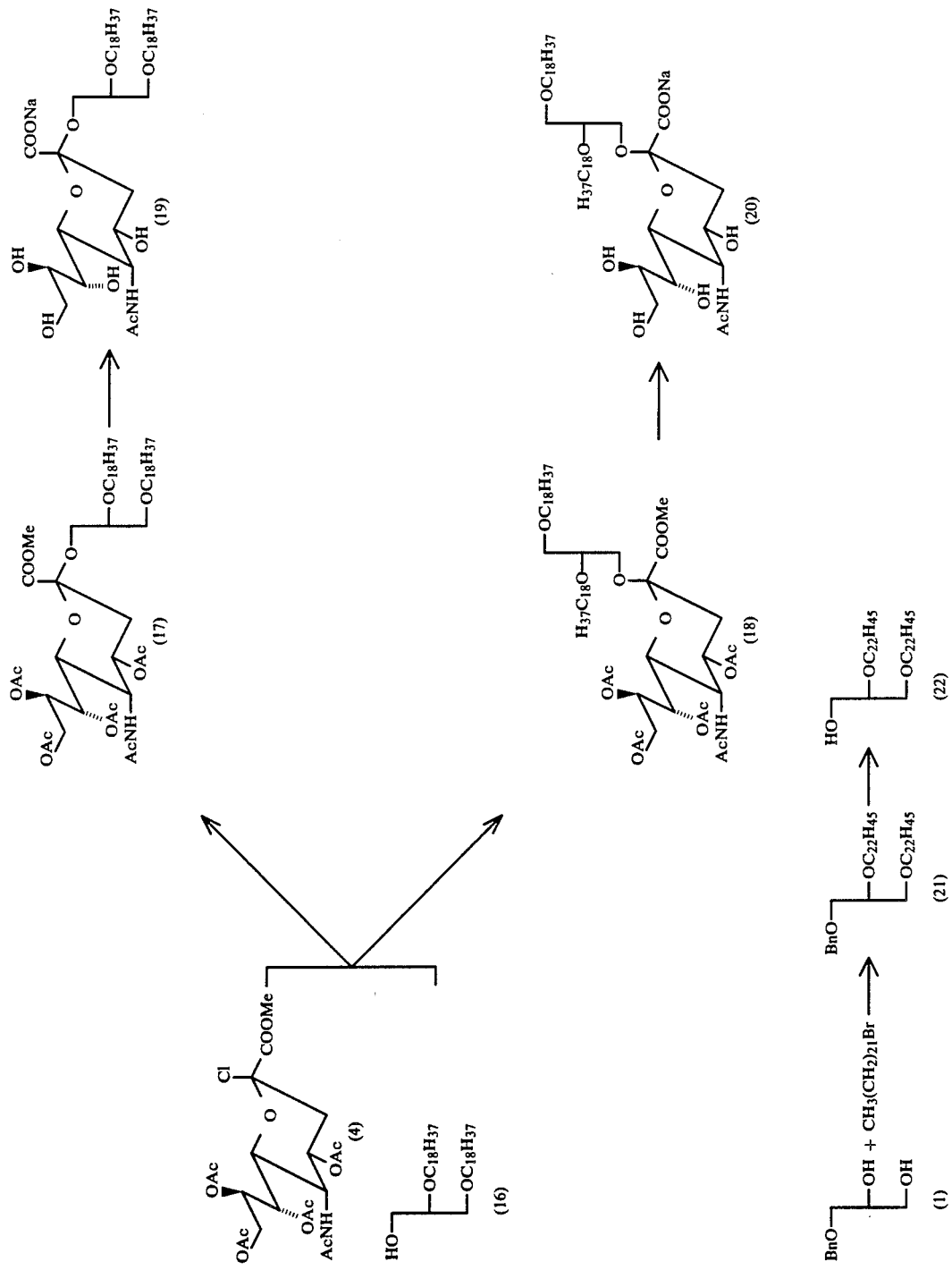

-continued
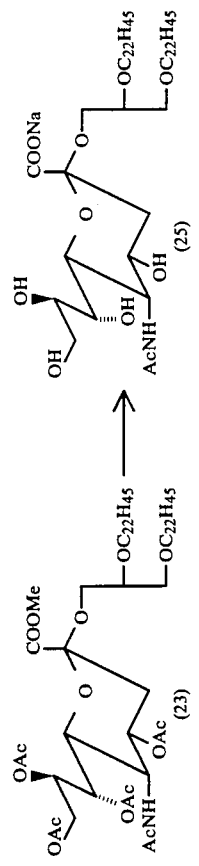
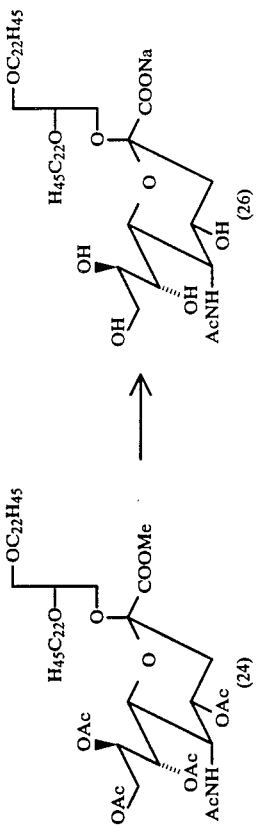
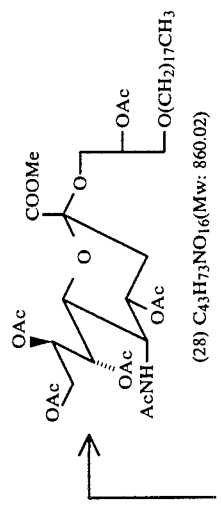
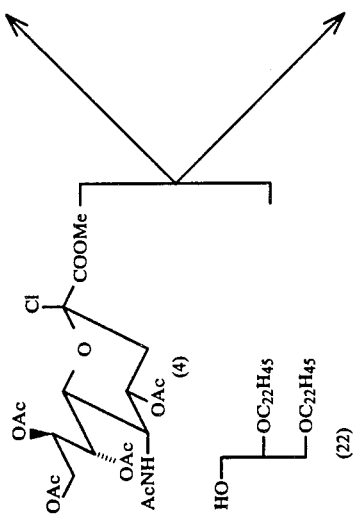

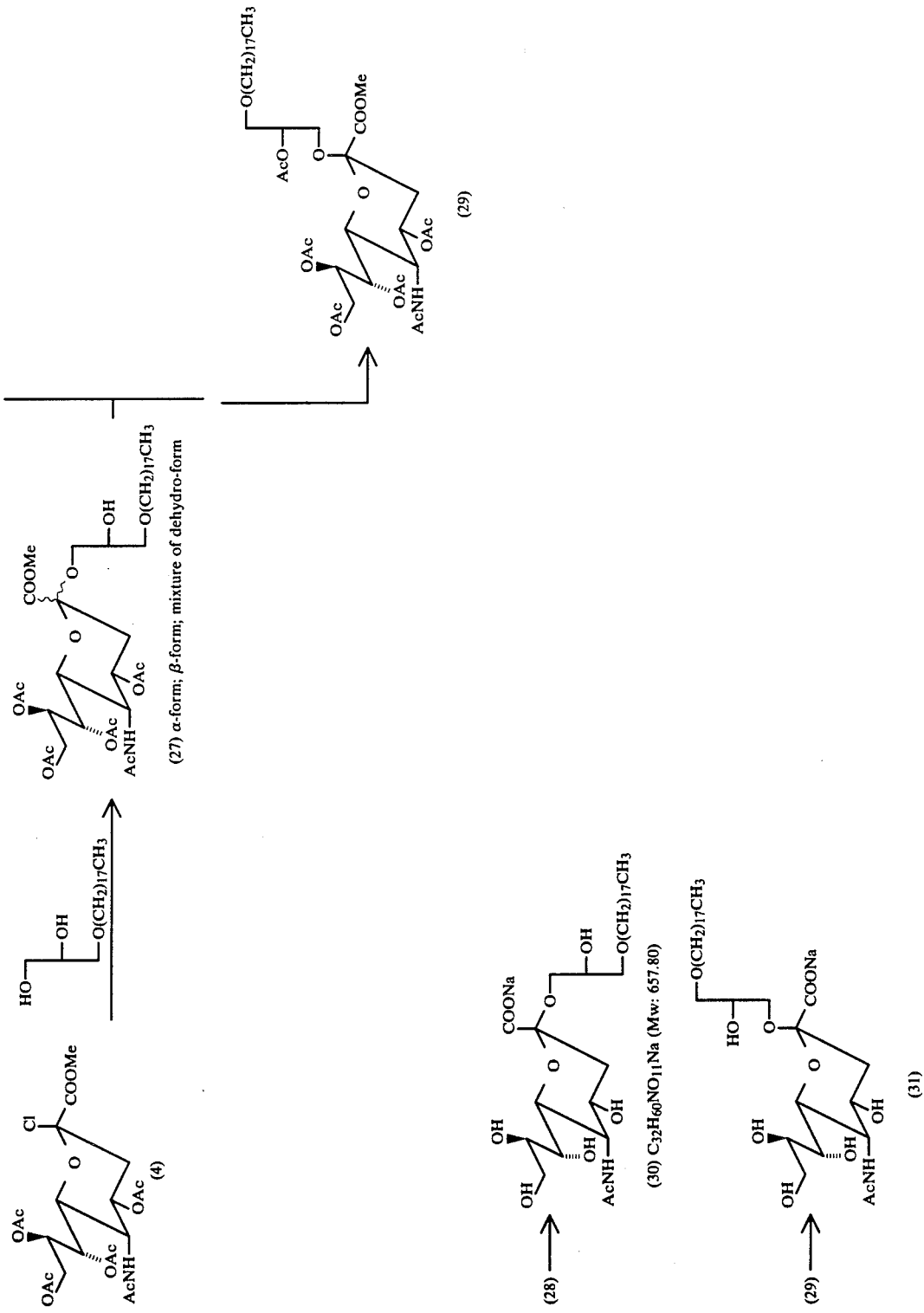

Thus, according to another aspect of the present invention, there is further provided a method for preparing novel sialocylglycerolipids represented by the following general formula (III):

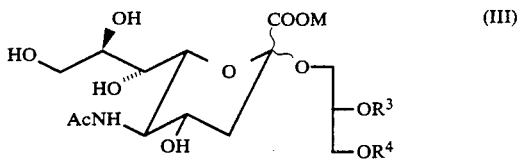

(wherein M is an alkali metal and $R^3$ and $R^4$ are the same as those defined above in connection with formula (I), which comprises treating a compound represented by the following general formula (II):

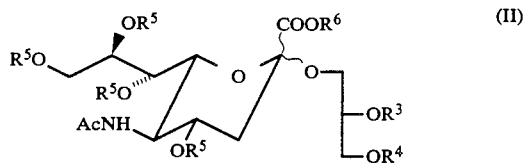

(wherein $R^5$ represents a group $CH_3CO-$, $R^6$ represents a hydrogen atom or a lower alkyl group and $R^3$ and $R^4$ are the same as those defined above) in an alkaline aqueous solvent.

In this regard, M is preferably a sodium atom, $R^3$ is preferably a hydrogen atom or a group $C_nH_{2n+1}-$ (n is an integer of 6, 10, 18 or 22) and $R^4$ is preferably a group $CH_mH_{2m+1}-$ (m is an integer of 6, 10, 18 or 22).

The hydrolyzation is preferably carried out in THF, under an alkaline condition as already mentioned above.

The present invention will hereunder be explained in more detail with reference to the following non-limitative Preparation Examples and Confirmation Examples.

EXAMPLE 1

(i) Synthesis of Compound (2) (1,2-Di-0-hexyl-3-0-benzyl-sn-glycerol)

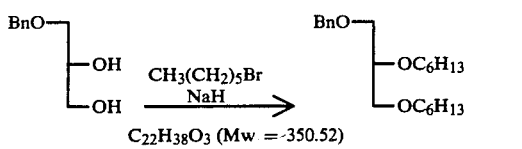

Compound (1) (3-0-benzyl-sn-glycerol; 1..3 g, 62.1 mmol) was dissolved in 150 ml of dimethylformamide (DMF), 7.5 g (187.5 mmol) of 60% NaH was added thereto in an ice-methanol bath and the mixture was stirred at room temperature for 20 minutes. Then 1-bromohexane (51.2 g) was added to the reaction mixture and stirred at room temperature for 6 hours. The reaction solution was filtered through cerite and filtrate was evaporated to dryness. The residue was again dissolved in ether and washed with 0.1N HCl solution, 2.5% sodium bicarbonate solution and dryed over anhydrous magnesium sulfate and concentrated to dryness. The residue was purified by column chromatography (Kieselgel 60 Merck Co.; eluent=hexane/ethyl acetate (50:1)) to obtain 26.3 g of compound (b 2).

(ii) Synthesis of 1,2-Di-0-hexyl-sn-glycerol (Compound (3))

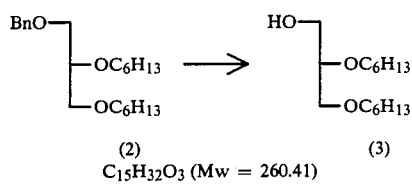

Compound (2) (26.3 g) was dissolved in 400 ml of ethyl acetate and 2.6 g of 10% palladium carbon was added to the solution and the solution was stirred at room temperature for 4 days under a nitrogen atmosphere. The palladium/carbon was filtered from the reaction solution, the solvent was evaporated off from the filtrate and the resultant residue was purified by column chromatography (Kieselgel 60; Merck Co.; eluent=$CHCl_3$ methanol system) to thus obtain 12.86 g (49.38 mmol) of compound (3). Overall yield calculated on the basis of the reactions (1)→(2)→(3) was 79.5%.

Physical Properties of Compound (3)

$[\alpha]_D^{30°}$ $^C$: $-17.1$ (c=1.1, $CHCl_3$) $^1H$ NMR (500 MHz; $CDCl_3$, Tetramethylsilane (TMS)): δH 0.886 (3H, t, J=7.0 Hz, $-CH_3$), 0.889 (3H, t, J=7.0 Hz, $-CH_3$), 1,271–1,370 (12H, m, $-CH_2 \times 6$), 1.530–1.604 (4H, m, $-OCH_2C\underline{H}_2 \times 2$), 3.405–3,746

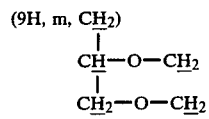

(iii) Synthesis of Compounds (5) and (6)

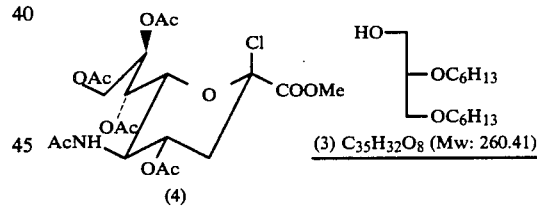

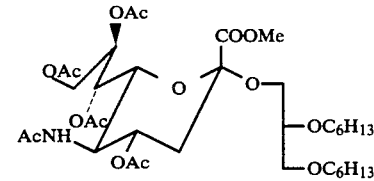

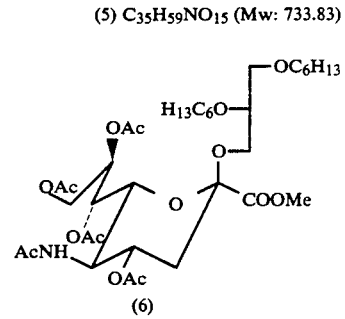

To a stirred mixture of powdered molecular sieves 4A (8.0 g) mercury (II) cyanide (2.87 g; 11.4 mmol), mercury (II) bromide (4.11 g; 11.4 mmol), compound (3) in CHCl₃ (100 ml) was added and stirred at room temperature under argon. The reaction solution was ice-cooled and 30 ml of a solution of compound (4) (8.0 g; 15.6 mmol) in chloroform was added thereto followed by stirring the solution at room temperature for 3 days. The reaction solution was filtered, the resultant residue was washed with chloroform followed by combining the filtrates and the washing and evaporating the solvent off therefrom. The residue obtained was purified by column chromatography (Wacogel C-300; Wako Chemicals; eluent=diethyl ether/ethanol system and toluene/ethyl acetate system) to obtain 2.6 g of the α-form (compound (5)), 1.51 g of the β-form (compound (6)), 2.0 g of the mixture thereof (6.11 g in all). The yield was 45.7%.

Physical Properties of Compound (5) 3-0-{Methyl-(5-acetamido -4,7,8,9-tetra-0-acetyl-3,5-dideoxy-3,5-dideoxy-α-D-glycero-D-galacto-2-nonulopyranosyl) -onato}-1,2-di-0-hexyl-sn-glycerol Rf=0.48 (Merck HPTLC; diethyl ether/ethanol =50/1) $[\alpha]_D^{30°\ C.} = -12.1$ (c =1.0, CHCl₃)

¹H NMR (500 MHz; CDCl₃, TMS): δ³H 0.886 (6H, t, —CH₃×2), 1.330 (12H, m, —CH₂—×6), 1.888 (3H, s, CH₃CONH—), 1.975 (1H, t, J =12.5 Hz, H—3ax), 2.025 (3H, s, CH₃COO—), 2.038 (3H, s, CH₃COO—), 2.131 (3H, s, CH₃COO—), 2.186 (3H, s, CH₃COO—), 2.602 (1H, dd, J =4.4, 12.8 Hz, H3eq), 3.791 (3H, s, -COOCH₃), 4.298 (1H, dd, j=2.6, 12.5 Hz, H—9),.4.853 (1H, ddd, H—4), 5.100 (1H, d, —CONH), 5.321 (1H, dd, J =1.5, 8.4 Hz, H—7), and 5.371 (1H, ddd, H—8).

Physical Properties of Compound (6) 3-0-{Methyl-(5-acetamido-4,7,8,9-tetra -0-acetyl-3,5-dideoxy-62-D-glycero-D-galacto-2-nonulopyranosyl) -onato}-1,2-di-0-hexyl-sn-glycerol RF=0.54 (Merck HPTLC; diethyl ether/ethanol =50/1) $[\alpha]_D^{30°\ C.} = -17.2$ (c=0.95, CHCl₃) ¹H NMR (500 MHz; CDCl₃, TMS): δH 0.889 (3H, t, —CH₃), 0.902 (3H, t, —CH₃), 1.310 (12H, m, —CH₂—×6), 1.882 (3H, s, CH₃CONH—), 1.900 (1H, t, J=12.8 Hz, H3ax), 2.013 (3H, s, CH₃COO—), 2.023 (3H, s, CH₃COO—), 2.064 (3H, s, CH₃COO—), 2.140 (3H, s, CH₃COO—), 2,454 (1H, dd, J=4.8, 12.8 Hz, H-3eq), 3,794 (3H, s, —CH₃COOCH₃), 4.722 (1H, dd, J =2.6, 12.5 Hz, H-9), 5.122 (1H, d, —CONH), 5.220 —5.290 (2H, H—4, H—8), and 5.378 (1H, dd, J=1.5, 4.4 Hz, H—7).

(iv) Synthesis of Compound (7)
3-0-{Sodium-(5-acetamido-3,5-dideoxy -α-D-glycero-D-galacto-2-nonulopyranosyl)onacto}- 1,2-di-0-hexyl-sn-glycerol

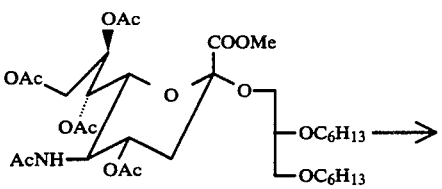

(5) C₃₅H₅₉NO₁₅ (Mw: 733.83)

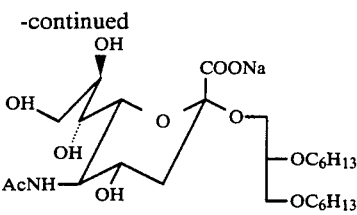

(7) C₂₆H₄₈NO₁₁Na (Mw: 573.65)

Compound (5) (1.69 g; 2.30 mmol) was dissolved in 3 ml of THF, 11 ml of 1N NaOH solution was added to the solution and it was stirred at room temperature for 7 hours. The reaction solution was neutralized with a cation exchange resin (Amberlite IRC-50; Rohm & Haas Co.) (pH=7) followed by filtering off the resin, washing the resin with distilled water, purifying the combined filtrate and washing by column chromatography (ODS 60Å YAMAMURA CHEMICAL LABORATORIES; 60/200 mesh; solvent=water, methanol), collecting methanol fractions, distilling off the solvent and then lyophilizing the residue to obtain 986.8 mg (1.72 mmol) of compound (7) as white powder. Yield=74.8%.

Physical Properties of Compound (7)
Rf=0.47 (Merck HPTLC; CHCl₃/methanol/CH₃COOH=5/3/0.5)
$[\alpha]_D^{+°\ C.} = -1.96$ (c=1.0, THF)
¹H NMR (500 MHz; D₂O, TS): δH 0.880 (6H, t, J=6.6 Hz, —CH₃×2), 1.340 (12H, s, —CH₂—×6), 1.580 (4H, m, —OCH₂CH₂—×2), 1.691 (1H, t, J=12.5 Hz, H—3ax), 2.730 (1H, dd, J=4.8, 12.5 Hz, H—3eq).

(V) Synthesis of Compound (8)
3-0-{Sodium-(5-acetamido-3,5-dideoxy-β-D-glycero-D-galacto-2-nonulopyranosyl)onato}-1,2-di-0-hexyl-sn-glycerol

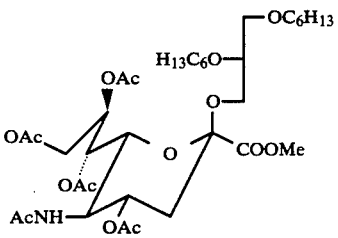

(6) C₃₅H₅₉NO₁₅ (Mw: 733.83)

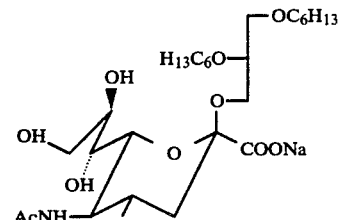

(8) C₂₆H₄₈NO₁₁Na (Mw: 573.65)

1.15 g (1.56 mmol) of compound (6) was dissolved in 3 ml of THF, then 10 ml of 1N NaOH solution was added thereto and the mixture was stirred at room temperature for 7 hours. The reaction solution was neutralized with a cation exchange resin (Amberlite IRC-50;

pH=7) followed by filtering off the resin, washing it with distilled water and purifying the combined filtrate and washing by column chromatography (ODS 60Å YAMAMURA CHEMICAL LABORATORIES; 60/200 mesh; solvent=water, methanol) collecting methanol fractions, distilling off the solvent and then lyophilizing the residue to obtain 748.0 mg (1.30 mmol) of compound (8) as white powder, Yield=83.3%.

Physical Properties of Compound (8)

Rf=0.54 (Merck HPTLC: CHCl$_3$/methanol/CH$_3$COOH=5/3/0.5)

$[\alpha]_D^{30°}$ $C.= -32.4$ (c=0.97, THF)

$^1$H NMR (500 MHz; D$_2$O, TSP): δH 0.880 (6H, —CH$_3$×2), 1.330 (12H, s, —CH$_2$—×6), 1.600 (4H, m, —OCH$_2$CH$_2$—×2), 1.626 (1H, t, J=12.8 Hz, H—3ax), 2.057 (3H, s, CH$_3$CONH—), 2.0408 (1H, dd, J=4.8, 12.8 Hz, H—3eq).

EXAMPLE 2

(i) Synthesis of Compound (9)
(1,2-di-0-decyl-3-0-benzyl-sn-glycerol)

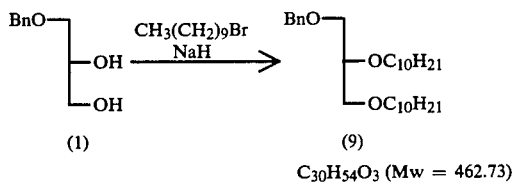

C$_{30}$H$_{54}$O$_3$ (Mw = 462.73)

13.6 g (74.7 mmol) of Compound (1) (3-0-benzyl-sn-glycerol) was dissolved in 20 ml of anhydrous dimethylformamide (DMF), 8.96 g (224.1 mmol) of 60% NaH was added thereto while cooling the solution in an ice-methanol bath and the solution was stirred at room temperature for 20 minutes. To the solution there was added 66.4 g of 1-bromodecane or 300.22 mmol of 1-chlorodecane and the resultant solution was stirred at room temperature for 6 hours. The reaction solution was filtered through a cerite layer followed by washing the residue with ether and evaporating the combined filtrate and washing to dryness under a reduced pressure. The residue was redissolved in ether, the solution was in turn washed with 0.1N HCl solution and 2.5% sodium bicarbonate solution followed by drying over anhydrous magnesium sulfate, distilling off the solvent and purifying the resulting residue by column chromatography (Kieselgel 60 Merck Co.; eluent=hexane/ethyl acetate 50:1) to obtain 33.5 g (it was confirmed, from TLC measurement, that this included 1-bromodecane). The product was used in the subsequent debenzylation without further purification.

(ii) Synthesis of Compound (10)
(1,2-di-0-decyl-sn-glycerol)

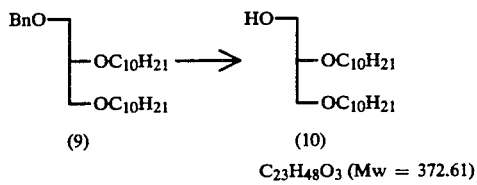

C$_{23}$H$_{48}$O$_3$ (Mw = 372.61)

Compound (9) (33.5 g; it was confirmed, from TLC measurement, that this included 1-bromodecane) was dissolved in 450 ml of ethyl acetate, 3.5 g of 10% palladium carrying active carbon was added thereto and the reaction solution was stirred at room temperature for 4 days in a hydrogen gas stream. The palladium-active carbon was filtered off from the solution, then the solvent was distilled off and the resultant residue was purified by column chromatography (Kieselgel 60 Merck Co.; eluent CHCl$_3$). The product thus obtained was recrystallized from petroleum ether to recover 26.2 g (70.31 mmol) of Compound (10). The yield was 94.1% which was calculated on the basis of the reactions (1)→(9)→(10).

Physical Properties of Compound (10) $[\alpha]_D^{30°}$ $C.= -11.7$ (c=1.1, CHCl$_3$) $^1$H NMR (500 MHz; CDCl$_3$, TMS); δH 0.880 (3H, t, J =7.0 Hz, —CH$_3$), 0.884 (3H, t, J =7.0 Hz, —CH$_3$), 1.200–1.400 (28H, m, —CH$_2$—×14), 1.500–1.600 (4H, m, —OCH$_2$CH$_2$—×2), 3.400–3.750

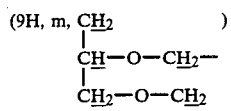

(iii) Synthesis of Compound (11)
3-0-{Methyl-(5-acetamido-4,7,8,9-tetra-0-acetyl-3,5-dideoxy-α-D-glycero-D-galacto-2-nonulopyranosyl)-onato}-1,2-di-0-decyl-sn-glycerol and Compound (12)

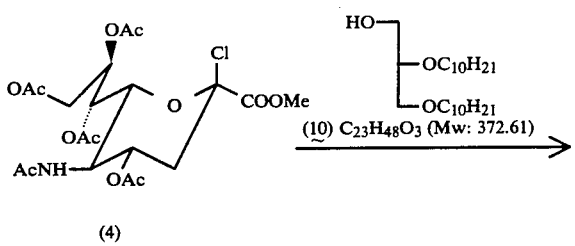

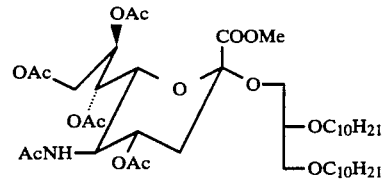

(11) C$_{43}$H$_{75}$NO$_{15}$ (846.04)

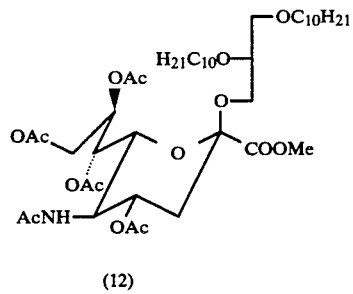

(12)

To a mixture of powdered molecular sieves 4A (4.0 g) mercury (II) cyanide (1.65 g; 6.5 mmol) and mercury (II) bromide (2.35 g; 6.5 mmol), compound (10) (4.0 g; 10.7 mmol) in CHCl$_3$ (80 ml) was added under argon and stirred for 2 hours at room temperature.

Then the reaction mixture was cooled in an ice bath at 0-5° C. and compound (4) (4.0 g; 7.8 mmol) in chloroform (20 ml was added and the solution was stirred at room temperature for 3 days. The reaction solution was filtered, the residue was washed with chloroform and the filtrate and the washing of the residue were concentrated in vacuo. The oily residue was purified by column chromatography (Wacogel C-300; eluent=diethyl ether/ethanol system and toluene/ethyl acetate system) to give 388.7 mg of the α-form (compound (11)), 469.5 mg of the β-form (compound (12)), 2.23 g of the mixture of these α- and β-form (3.09 g in all). The yield was 46.8%.

Physical Properties of Compound (11)

Rf=0.54 (Merck HPTLC; diethyl ether/ethanol =50/1) $[\alpha]_D^{30°\ C.} = -9.9$ (c=1, CHCl$_3$) $^1$H NMR (500 MHz; CDCl$_3$, TMS): δH 0.878 (6H, t, J =7.0 Hz, —CH$_3$ ×2), 1.810 (28H, m, —CH$_2$—×14), 1.881 (3H, s, CH$_3$CONH—), 1.975 (1H, t, J =12.5 Hz, H -3ax), 2.025 (3H, s, CH$_3$COO—), 2.038 (3H, s, CH$_3$COO—), 2.131 (3H, s, CH$_3$COO—), 2.137 (3H, s, CH$_3$COO—), 2.602 (1H, dd, J=4.8, 12.8 Hz, H- 3eq), 3.791 (3H, s, —COOCH$_3$), 4.299 (1H, dd, J =2.6, 12.5 Hz, H-9), 4.856 (1H, ddd, H-4), 5.102 (1H, d, —CONH—), 5.321 (1H, dd, H-7) and 5.371 (1H, ddd, H-8).

Physical Properties of Compound (12) 3-0-{Methyl-(5-acetamido-4,7,8,9-tetra-0-acetyl-3,5-dideoxy-β-D-glycero-D-galacto-2-nonulopyranosyl)-onato}-1,2-di-0-decyl -sn-glycerol Rf=0.68 (Merck HPTLC; diethyl ether/ethanol =50/1) $[\alpha]_D^{30°\ C.} = -13.3$ (c=1, CHCl$_3$)

1H NMR (500 MHz; CDCl$_3$, TMS): δH 0.881 (6H, t, —CH$_3$2), 1.285 (28H, m, —CH$_2$—×14), 1.882 (3H, s, CH$_3$CONH—), 2.012 (3H, s, CH$_3$COO—), 2.023 (3H, s, CH$_3$COO—), 2.063 (3H, s, CH$_3$COO—), 2.141 (3H, s, CH$_3$COO—), 2.454 (1H, dd, J 4.9, 13.2 Hz, H-3eq), 3.794 (3H, s, —COOCH$_3$), 4.723 (1H, dd, J =2.4, 12.2 Hz, H-9), 5.138 (1H, d, —CONH—), 5.200-5.290 (2H, H-4, H-8), and 5.376 (1H, H-7).

(iv) Synthesis of Compound (13)
3-0-{Sodium-(5-acetamido-3,5-dideoxy -α-D-glycero-D-galacto-2-nonulopyranosyl)onato}-1,2-di-0-decyl-sn-glycerol

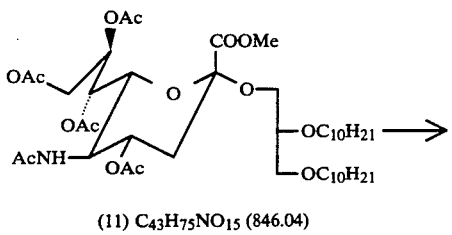

(11) C$_{43}$H$_{75}$NO$_{15}$ (846.04)

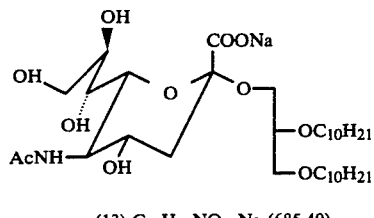

(13) C$_{34}$H$_{64}$NO$_{11}$Na (685.49)

Compound (11) (343.3 mg; 0.41 mmol) was dissolved in 1 ml of THF, then 3 mol of 1N NaOH solution was added thereto and the resulting solution was stirred at room temperature for 5 hours. The reaction solution was neutralized with a cation exchange resin (Amberlite IRC-50 Rohm & Haas Co.) (pH =7), the resin was filtered off and washed with distilled water, and the combined filtrate and washings were purified by column chromatography (ODS 60Å; YAMAMURA CHEMICAL LABORATORIES; 60/200 mesh; solvent=water, methanol). The methanol fractions were collected, the solvent was distilled therefrom and the residue was lyophilized to obtain 218.9 mg (0.32 mmol) of compound (13). The yield was 78.0%.

Physical Properties of Compound (13)

Rf=0.54 (Merck HPTLC; chloroform/methanol/acetic acid=5/3/0.5)

$[\alpha]_D^{30°\ C.} = -2.25$ (c=0.93, THF)

$^1$NMR (500 MHz; D$_2$O, TSP): δH 0.885 (6H, m, —CH$_3$×2), 1.310 (28H, s, —CH$_2$—×14), 1.583 (4H, br.s, —OCH$_2$CH$_2$—×2 ), 1.700 (1H, t, J=12.5 Hz, H-3ax), 2.049 (3H, s, CH$_3$CONH—) and 2.733 (1H, br.d, J=8.4 Hz, H-3eq).

(v) Synthesis of Compound (14)
3-0-{Sodium-(5-acetamido-3,5-dideoxy-β-D-glycero-D-galacto-2-nonulopyranosyl)-onato}-1,2-di-0-decyl-sn-glycerol

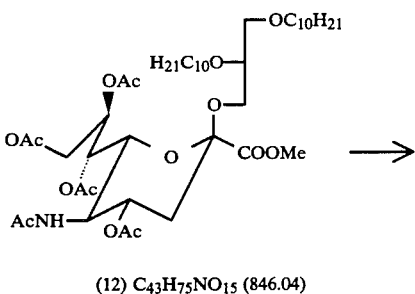

(12) C$_{43}$H$_{75}$NO$_{15}$ (846.04)

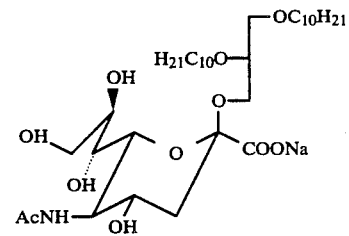

(14) C$_{34}$H$_{64}$NO$_{11}$Na (685.49)

Compound (12) (397.0 mg; 0.47 mmol) was dissolved in 1 ml of THF, then 3.5 ml of 1N NaOH solution was added thereto and the solution was stirred at room temperature for 5 hours. The reaction solution was neutralized with Amberlite IRC-50 (pH=7), the resin was filtered and washed with distilled water, the combined filtrate and washings were purified by column chromatography (ODS 60Å; YAMAMURA CHEMICAL LABORATORIES; 60/200 mesh; solvent=water, methanol), the methanol fractions were collected, the solvent was distilled from the fractions and the residue was lyophilized to obtain 155.0 mg (0.23 mmol) of compound (14) as white powder. The yield was 48.9%.

Physical Properties of Compound (14)

Rf=0.68 (Merck HPTLC; chloroform/methanol/acetic acid5/3/0.5)

$[\alpha]_D^{30°\ C.} = -47.7$ (c=1, THF $^1$H NMR (500 MHz; D$_2$O, TSP): δH 0.897 (6H, m, —CH$_3$×2), 1.323 (28H, s, —CH$_2$—×14), 1.602 (4H, br.s, —OCH$_2$CH$_2$—×2), 2.074 (3H, CH$_3$CONH—) and 2.430 (1H, m, H-3eq).

EXAMPLE 3

(i) Synthesis of Compound (15)
(1,2-di-0-benzyl-sn-glycerol)

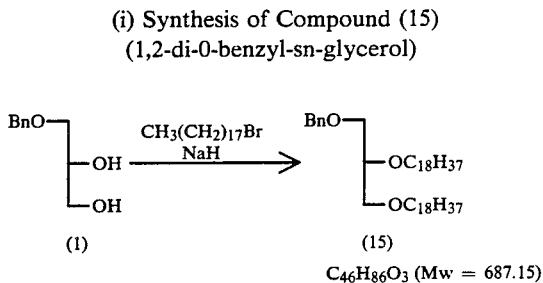

C$_{46}$H$_{86}$O$_3$ (Mw = 687.15)

Compound (1) (4.0 g; 22.0 mmol; 3-0-benzyl-sn-glycerol) was dissolved in 10 ml of DMF, 2.7 g (66.0 mmol) of 60% NaH was added thereto and the resulting solution was stirred at room temperature for 10 minutes. To the solution there was added 25 g of 1-bromooctadecane or 75.0 mmoles of 1-chlorooctadecane and the solution was stirred at room temperature for 6 hours. The reaction solution was filtered through a cerite layer, the resultant residue was washed with ether and the combined filtrate and washings were evaporated to dryness under a reduced pressure. The residue was redissolved in ether, washed with 0.1N HCl solution and 2.5% potassium bicarbonate solution, dried over anhydrous magnesium sulfate and then the solvent was distilled to obtain 16.0 g of oily material. The oily material was purified by column chromatography (Wacogel C-300, 550 g; toluene/ether system) to thus obtain 9.25 g (13.46 mmol) of compound (15). The yield was 61.3%. This was used in the subsequent process without further purification.

(ii) Synthesis of Compound (16)
(1,2-di-0-octadecyl-sn-glycerol)

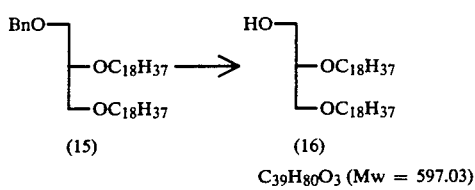

C$_{39}$H$_{80}$O$_3$ (Mw = 597.03)

Compound (15) (8.8 g; 13.0 mmol) was dissolved in 150 ml of ethyl acetate, 800 mg of 10% palladium carrying active carbon was added thereto and the solution was stirred at room temperature for 40 hours in a hydrogen gas stream.

The palladium-active carbon was filtered and the solvent was distilled from the filtrate to obtain 6.21 g (10.4 mmol) of Compound (16). The yield was 79.8%.

Physical Properties of Compound (16)

[α]$_D^{30°}$ C. = −7.5 (c=1, CHCl$_3$)

$^1$H NMR (500 MHz, CHCl$_3$; TMS): δH 0.880 (6H, t, J=7.0 Hz, —CH$_3$×2), 1.150–1.380 (60H, m —CH$_2$—×90), 1,540–1.590 (4H, m, —OCH$_2$CH$_2$—×2), 3.400–3.750

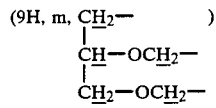
(9H, m, CH$_2$—
CH—OCH$_2$—
CH$_2$—OCH$_2$—)

(iii) Synthesis of Compound (17)
3-0-{Methyl-(5-acetamido-4,7,8,9-tetra-0-acetyl-3,5-dideoxy-60-D-glycero-D-galacto-2-nonulopyranosyl)-onato}-1,2-di-0-octadecyl-sn-glycerol and compound (18)

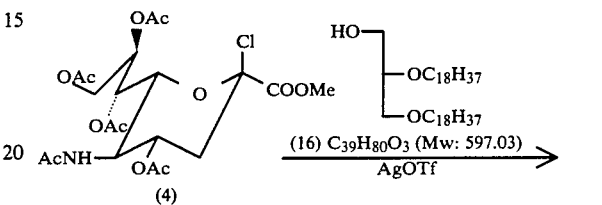

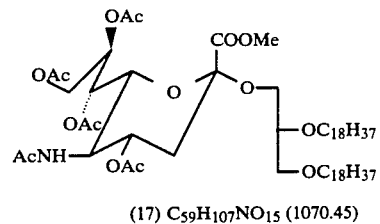

(17) C$_{59}$H$_{107}$NO$_{15}$ (1070.45)

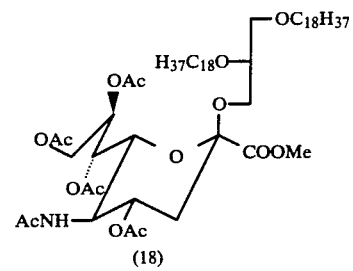

(18)

Powdery Molecular Sieve 4A (5.0 g) which had been dried under reduced pressure while heating the same at 180° C. was suspended in 50 ml of THF, or then 2.82 g (4.72 mmol) of compound (16) was added thereto and the resulting solution was stirred at room temperature for 30 minutes. The reaction solution was cooled in an ice-methanol bath, 3.65 g (14.23 mmol) of AgOTf, or a combination of mercury (II) cyanide and mercury bromide was added to the solution in an argon gas stream while shielding the light followed by stirring it for 15 minutes, further adding 20 ml of a solution of 4.83 g (9.49 mmol) of compound (4) in THF and stirring at room temperature for 3 hours. The reaction solution was filtered, the residue was washed with chloroform and the solvent was distilled from the combined filtrate and washings. The resultant residue was dissolved in chloroform, washed with saturated sodium bicarbonate solution and saturated sodium chloride solution, then dried over anhydrous magnesium sulfate and the solvent was distilled off. The resultant residue was purified by column chromatography (Wacogel C-300; eluent-=diethyl ether/toluene/ethyl acetate system) to obtain 640 mg of the α-form (Compound (17)), 221 mg of the β-form (Compound (18)) and 515 mg of a mixture of the α- and β-form. The yield calculated on the basis of Compound (16) was 27.3%.

Physical Properties of Compound (17)

Rf=0.70 (Merck HPTLC; diethyl ether/ethanol=50/1) $[\alpha]_D^{30°\ C.} = -8.4$ (c=1, CHCl$_3$)

$^1$H NMR (500 MHz; CDCl$_3$, TMS): δH 0.879 (6H, t, —CH$_3$×2), 1.315 (60H, m, —CH$_2$—×30), 1.880 (3H, s, CH$_3$CONH—), 1.975 (1H, t, J=12.5 Hz, H-3ax), 2.025 (3H, s, CH$_3$COO—), 2.038 (3H, s, CH$_3$COO—), 2.132 (3H, s, CH$_3$COO—), 2.136 (3H, s, CH$_3$COO—), 2.603 (1H, dd, J=4.4, 12.8 Hz, H-3eq), 3.789 (3H, s, —COOCH$_3$), 4.308 (1H, dd, J=2.9, 12.5, Hz, H-9), 4.856 (1H, ddd, H-4), 5.254 (1H, d, —CONH—), 5.328 (1H, dd, H-7) and 5.371 (1H, ddd, H-8).

Physical Properties of Compound (18) 3-0-{Methyl-(5-acetamido -4,7,8,9-tetra-0-acetyl-3,5-dideoxy-62-D-glycero-D-galacto-2-nonulopyranosyl) -onato}-1,2-di-0-octadecyl-sn-glycero Rf=0.80 (Merck HPTLC; diethyl ether/ethanol=50/1)

$[\alpha]_D^{30°\ C.} = -10.8$ (c=1, CHCl$_3$)

$^1$H NMR (500 MHz; CDCl$_3$, TMS):δH 0.880 (6H, t, —CH$_3$×2), 1.250 (60H, m, —CH$_2$—×30), 1.881 (3H, s, CH$_3$CONH—), 1.900 (1H, t, J=11.7 Hz, H-3ax), 2.011 (3H, s, CH$_3$COO—), 2.022 (3H, s, CH$_3$COO—), 2.063 (3H, s, CH$_3$COO—), 2.140 (3H, s, CH$_3$COO—), 2.454 (1H, dd, J=4.8, 12.8 Hz, H-3eq), 3.793 (3H, s, —COOCH$_3$), 4.726 (1H, dd, J=2.6, 12.5 Hz, H-9), 5.138 (1H, d, —CONH—), 5.200-5.300 (2H, H-4, H-8) and 5.376 (1H, H-7).

(iv) Synthesis of Compound (19)
3-0-{Sodium-(5-acetamido-3.5-dideoxy -α-D-glycero-D-galacto-2-nonulopyranosyl)-onato}-1,2-di-0-octadecyl-sn-glycerol

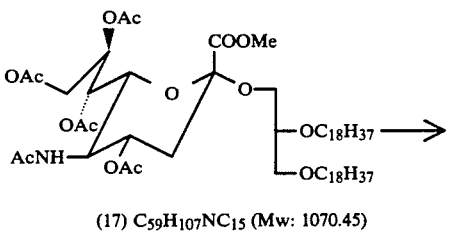

(17) C$_{59}$H$_{107}$NC$_{15}$ (Mw: 1070.45)

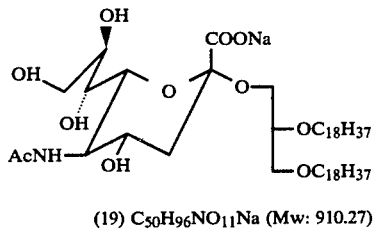

(19) C$_{50}$H$_{96}$NO$_{11}$Na (Mw: 910.27)

Compound (17) (520.0 mg; 0.49 mmol) was dissolved in 3 ml of THF, then 6 ml of 1N NaOH solution was added thereto and the solution was stirred at room temperature for 5 hours. The reaction solution was neutralized with Amberlite IRC-50 (pH=7), the resin was filtered off and was washed with distilled water, the combined filtrate and washings were purified by column chromatography (ODS 60Å, YAMAMURA CHEMICAL LABORATORIES; 60/200 mesh, solvent water, methanol) followed by collecting the methanol fractions, distilling off the solvent and lyophilizing the residue to obtain 362 mg (0.40 mmol) of compound (19) as white powder. The yield was 81.6%.

Physical Properties of Compound (19)

Rf=0.60 (Merck HPTLC; chloroform/methanol/acetic acid=5/3/0 5)

$[\alpha]_D^{30°\ C.} = -1.98$ (c=0.96, THF)

$^1$H NMR (500 MHz, DMSOd$_6$+D$_2$O, TMS): δH 0.852 (6H, t, J=7.0 Hz, —CH$_3$×2), 1.100-1.350 (60H, m, —CH$_2$—×30), 1.400-1.500 (4H, m, —OCH$_2$CH$_2$—×2) and 1.896 (3H, s, CH$_3$CONH—)

(v) Synthesis of Compound (20)
3-0-{Sodium-(5-acetamido3,5-dideoxy-8-D-glycero-D-galacto-2-nonulopyranosyl)onato}-1,2-di-0-octadecyl-sn-glycerol

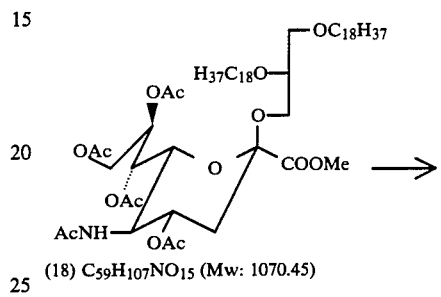

(18) C$_{59}$H$_{107}$NO$_{15}$ (Mw: 1070.45)

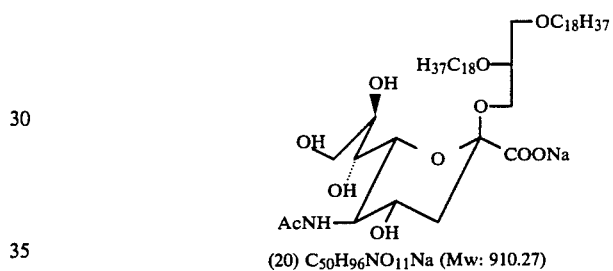

(20) C$_{50}$H$_{96}$NO$_{11}$Na (Mw: 910.27)

Compound (18) (140.0 mg; 0.13 mmol) was dissolved in 2 ml of THF, 4 ml of 1N NaOH solution was added to the solution and then the solution was stirred at room temperature for 6 hours. The reaction solution was neutralized with Amberlite IRC-50 (pH=7), then the resin was filtered and washed with distilled water, the combined filtrate and washings were purified by column chromatography (ODS 60Å, YAMAMURA CHEMICAL LABORATORIES; 60/200 mesh, solvent=water, methanol) followed by collecting the methanol fractions, distilling off the solvent and lyophilizing the residue to obtain 50 mg (0.05 mmol) of compound (20) as white powder. The yield was 38.5%.

Physical Properties of Compound (20)

Rf=0.70 (Merck HPTLC; chloroform/methanol/acetic acid=5/3/0.5)

$^1$H NMR (500 MHz, DMXOd$_6$+D$_2$O, TMS): δH 0.853 (6H, t, J=7.3 Hz, —CH$_3$×2), 1.100-1.360 (60H, m, —CH$_2$—×30), 1.400-1.500 (4H, m, —OCH$_2$CH$_2$—×2), 1.882 (3H, s, CH$_3$CONH—) and 2.122 (1H, m, H-3eq).

EXAMPLE 4

(i) Synthesis of Compound (21)

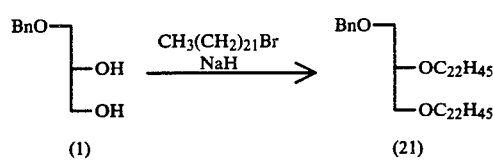

-continued

C54H102O3 (Mw = 799.36)

Compound (1) (5.8 g; 32.0 mmol) was dissolved in 20 ml of anhydrous dimethylformamide (DMF), then 3.1 g (96.0 mmol) of 60% NaH was added thereto and the solution was stirred at room temperature for 10 minutes. To the solution there was added 50.0 g (128.4 mmol) of 1-bromodocosane and the solution was stirred at room temperature for 6 hours. The reaction solution was filtered through a cerite layer, the residue was washed with ether and the combined filtrate and washings were evaporated to dryness under reduced pressure. The residue was redissolved in ether, the resultant solution was washed with 0.1N HCl solution and 2.5% sodium bicarbonate solution and dried over anhydrous magnesium sulfate and the solvent was distilled off to obtain 28.3 g of oily material. The oily material was purified by column chromatography (800 g of Wacogel C-300; eluent=hexane/ethyl acetate=50/1) to thus obtain 17.3 g of compound (21) (this contained 1-bromodocosane). The product was used in the subsequent step without further purification.

(ii) Synthesis of Compound (22)

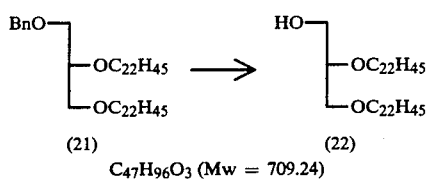

(21)      (22)

C47H96O3 (Mw = 709.24)

Compound (21) (17.3 g; this contained 1-bromodocosane) was dissolved in 200 ml of a mixed solvent of ether/ethyl acetate/methanol (1/1/1), 1.7 g of 10% palladium supported on active carbon was added thereto and the solution was stirred at room temperature for 2 days in a hydrogen gas stream. The reaction solution was filtered, the resultant residue was washed with chloroform and the solvent was distilled from the combined filtrate and washings. The residue obtained was purified by column chromatography (Merck Co., Kieselgel 60; eluent=hexane/ethyl acetate (5:1 to 3:1)), the solvent was distilled off and the residue was recrystallized from hexane/ether to obtain 14.5 g (20.4 mmol) of compound (22). The overall yield (from compound (1) to compound (22)) was 63.4%.

Physical Properties of Compound (22)

$^1$H NMR (500 MHz, CDCl$_3$, TMS): δH 0.880 (6H, t, J=7.0 Hz, —CH$_3$×2), 1.150–1.450 (76H, m, —CH$_2$—×38), 1.500–1.650 (4H, m, —OCH$_2$C$\underline{H}_2$—×2) and 3.400–3.750

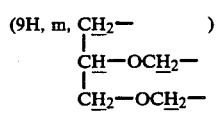

(9H, m, C$\underline{H}_2$—
C$\underline{H}$—OC$\underline{H}_2$—
C$\underline{H}_2$—OC$\underline{H}_2$— )

(iii) Synthesis of Compounds (23) and (24)

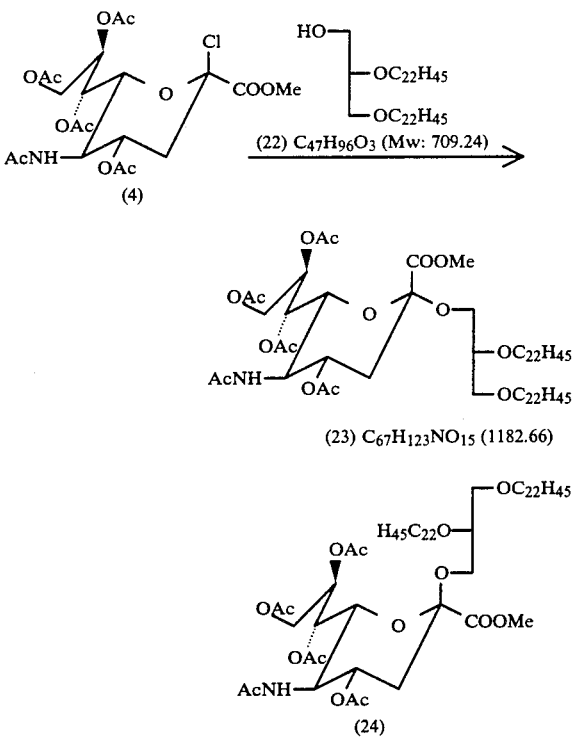

Powdery Molecular Sieve 4A (7.1 g) which had been dried under a reduced pressure while heating the same at 180° C., mercury (II) cyanide (2.06 g; 8.1 mmol) and mercury (II) bromide (2.94 g; 8.1 mmol) were suspended in 60 ml of anhydrous chloroform, then compound (22) (5.31 g; 7.5 mmol) was added thereto and the reaction solution was stirred at room temperature for 2 hours in an argon gas stream. The reaction solution was ice-cooled, 10 ml of a solution of compound (4) (2.55 g; 5.0 mmol) in chloroform was added thereto and the solution was stirred at room temperature for 24 hours. The reaction solution was filtered, the resultant residue was washed with chloroform and the solvent was distilled from the combined filtrate and washing. The resulting residue was purified by column chromatography (Wacogel C-300, eluent diethyl ether/ethanol and toluene/ethyl acetate systems) to thus obtain 1.95 g of the α-form (compound (23)), 1.38 g of the β-form (compound (24)) and 1.0 g of the mixture thereof (the total yield was 4.33 g). The yield was 73.2%.

Physical Properties of Compound (23)

Rf=0.68 (Merck HPTLC; diethyl ether/ethanol=24/1) $^1$H NMR (500 MHz; CDCl$_3$, TMS): δH 0.880 (6H, t, J=7.0 Hz, —CH$_3$×2), 1.253 (76H, m, —CH$_2$—×38), 1.882 (3H, s, CH$_3$CONH—), 1.976 (1H, t, J=12.5 Hz, H-3ax), 2.025 (3H, s, CH$_3$COO—), 2.132 (3H, s, CH$_3$COO—), 2.137 (3H, s, CH$_3$COO—), 2.601 (1H, dd, J=4.8, 12.8 Hz, H-3eq), 3.791 (3H, s, —COOCH$_3$), 4.298 (1H, dd, J =2.9, 12.5 Hz, H-9), 4.852 (1H, ddd, H-4), 5.120 (1H, d, —CONH—), 5.322 (1H, dd, H-7) and 5.371 (1H, ddd, H-8).

Physical Properties of Compound (24) Rf=0.73 (Merck HPTLC; diethyl ether/ethanol =24/1)

$^1$H NMR (500 MHz; CDCl$_3$, TMS): δH 0.880 (6H, t, —CH$_3$×2), 1.253 (76H, m, —CH$_2$—×38), 1.882 (3H, s, CH$_3$CONH—), 1.898 (1H, t,

J=11.7 Hz, H-3ax), 2.013 (3H, x, CH₃COO—), 2.024 (3H, s, CH₃COO—), 2.064 (3H, s, CH₃COO—), 2.143 (3H, s, CH₃COO—), 2.455 (1H, dd, J=4.8, 12.8 Hz, H-3eq), 3.794 (3H, s, —COOCH₃), 4.468 (1H, dd, J=2.6, 12.5 Hz, H-9) and 5.379 (1H, dd, H-7).

(iv) Synthesis of Compounds (25)

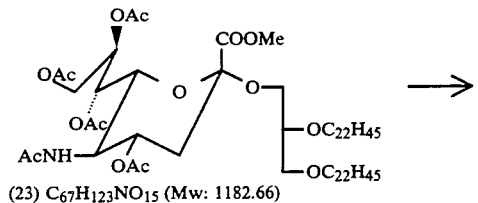

(23) C$_{67}$H$_{123}$NO$_{15}$ (Mw: 1182.66)

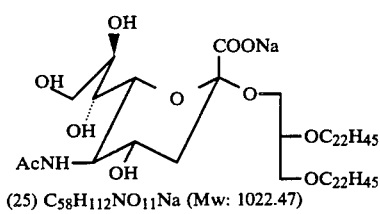

(25) C$_{58}$H$_{112}$NO$_{11}$Na (Mw: 1022.47)

Compound (23) (1.59 g; 1.35 mmol) was dissolved in about 30 ml of THF, then 11 ml of 1N NaOH solution was added thereto and the solution was stirred at room temperature for 7 hours. The reaction solution was neutralized with Amberlite IRC-50 (pH=7), followed by filtering off the resin, washing the resin with distilled water, purifying the combined filtrate and washings through a column packed with (ODS 60Å, YAMAMURA CHEMICAL LABORATORIES; 60/200 mesh; solvent=water, methanol), collecting the methanol fractions, distilling off the solvent and lyophilizing the resultant residue to obtain 1.19 g of compound (25) as white powder. The yield was 86.7%

Physical Properties of Compound (25)

¹H NMR (500 MHz; CDCl₃+CD₃OD (1:1), TMS): δH 0.889 (6H, t, j=7.3 Hz, —CH₃×2), 1.150–1.400 (76H, m, —CH₂—×38), 1.500–1.700 (4H, m, —OCH₂CH₂—×2) and 2.030 (3H, s, CH₃CONH—).

(v) Synthesis of Compound (26)

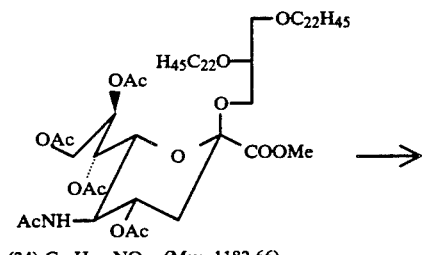

(24) C$_{67}$H$_{123}$NO$_{15}$ (Mw: 1182.66)

-continued

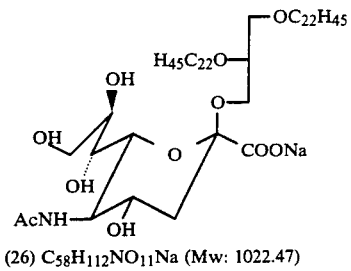

(26) C$_{58}$H$_{112}$NO$_{11}$Na (Mw: 1022.47)

Compound (24) (1.04 g; 0.88 mmol) was dissolved in about 20 ml of THF, then 5.3 ml of 1N NaOH solution was added thereto and the solution was stirred at room temperature for 7 hours. The reaction solution was neutralized with Amberlite IRC-50 (pH =7) followed by filtering off the resin, washing the resin with distilled water, purifying the combined filtrate and washings by column chromatography (ODS 60Å, YAMAMURA CHEMICAL LABORATORIES; 60200 mesh, solvent=water, methanol), collecting the methanol fractions, distilling off the solvent and lyophilizing the resultant residue to obtain 748 mg of compound (26) as white powder. The yield was 83.6%.

Physical Properties of Compound (26)

¹NMR (500 MHz, CDCl₃+CD₃OD (1:1), TMS): δH 0.888 (6H, t, J=7.0 Hz, —CH₃×2), 1.100–1.450 (76H, m, —CH₂—×38), 1.500–1.700 (4H, m, —OCH₂CH₂—×2), 2.046 (3H s, CH₃CONH—).

EXAMPLE 5

(i) Synthesis of Compounds (28) and (29)

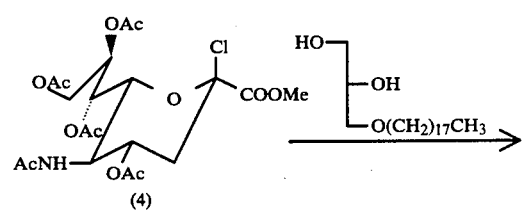

(27) →

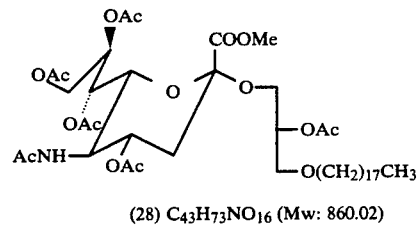

(28) C$_{43}$H$_{73}$NO$_{16}$ (Mw: 860.02)

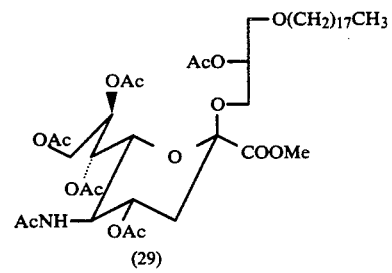

(29)

Powdery Molecular Sieve 4A (5.0 g) which had been dried under a reduced pressure while heating the same at 180° C., mercury (II) bromide (2.09 g; 5.8 mmol) and mercury (II) cyanide (1.46 g; 5.8 mmol) or silver trifluoromethane sulfonate were suspended in 50 ml of anhydrous chloroform, THF of dichloromethane, then 0.92 g (2.7 mmol) of butyl alcohol (S-form) was added to the suspension and it was stirred at room temperature for 2 hours in an argon gas stream.

The reaction solution was ice-cooled followed by adding 15 ml of a solution of compound (27) (2.03 g; 4.0 mmol) in anhydrous chloroform thereto and stirring the solution at room temperature for 3 days. The reaction solution was filtered, the residue was washed with chloroform and the solvent was distilled from the combined filtrate and washing. The resultant residue was purified by column chromatography (Wacogel C-300; eluent = diethyl ether/ethanol system and toluene/methanol system) to obtain 1.2 g of compound (27) (a mixture of α-, β- and dehydro-forms).

To compound (27) there were added 30 ml of acetic acid anhydride and 40 ml of anhydrous pyridine and the solution was stirred at room temperature for 18 hours. The reaction solution was evaporated to dryness under reduced pressure followed by redissolving the resultant residue in ethyl acetate, washing the solution with saturated sodium bicarbonate solution and saturated sodium chloride solution, drying the solution over anhydrous magnesium sulfate and distilling off the solvent to obtain 1.6 g of residue.

The resultant residue was purified by column chromatography (Merck Co., Kieselgel 60; eluent=diethyl ether/methanol (60/1)) and then passed through a lobar column Type C (eluent=toluene/methanol (15:1)) to obtain 193.4 mg of the α-form (compound (28)), 171.3 mg of the β-form (compound (29)) and 513.1 mg of the mixture thereof (877.8 mg in all). The yield calculated on the basis of butyl alcohol was 37.8%.

Physical Properties of α-form
$^1$H NMR (500 MHz, CDCl$_3$, TMS): δH 0.884 (3H, t, —CH$_3$), 1.888 (3H, s, —NHCOCH), 1.949 (1H, t, H-3ax), 2.586 (1H, dd, H-3eq), 3.817 (3H, s, —COOCH$_3$) and 1.870 (1H, m, H-4).

Physical Properties of β-form
$^1$H NMR (500 MHz, CDCl$_3$, TMS): δH 0.878 (3H, t, —CH$_3$), 1.885 (3H, s, —NHCOCH$_3$), 1.898 (1H, t, H-3ax), 2.465 (1H, dd, H-3eq), 3.800 (3H, s, —COOCH$_3$) and 5.219 (1H, m, H-4).

(ii) Synthesis of Compound (30)

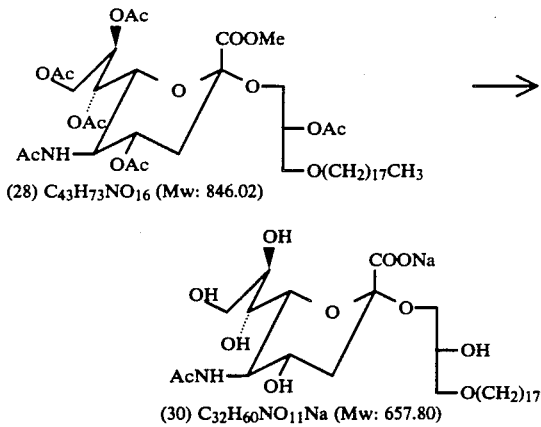

To compound (28) (163.4 mg; 0.19 mmol) there was added 1.14 ml of 1N NaOH solution and the solution was stirred at room temperature for 8 hours. The reaction solution was neutralized with a cation exchange resin (Amberlite IRC-50; pH =7) followed by filtering off the resin, washing the resin with distilled water, purifying the combined filtrate and washing by column chromatography (ODS 60Å, YAMAMURA CHEMICAL LABORATORIES, 60/200 mesh, solvent=water, methanol), collecting the methanol fractions, distilling off the solvent and lyophilizing the residue obtained to form 112.3 mg of compound (30) as white powder. The yield was 89.9%.

Physical Properties of Compound (30)
$^1$NMR (500 MHz, C$_5$D$_5$N, TMS): δH 0.883 (s, —CH$_3$), 2.066 (s, —NHCOCH$_3$), 2.349 (t, H-3ax) and 3.737 (q, H-3eq).

(iii) Synthesis of Compound (31)

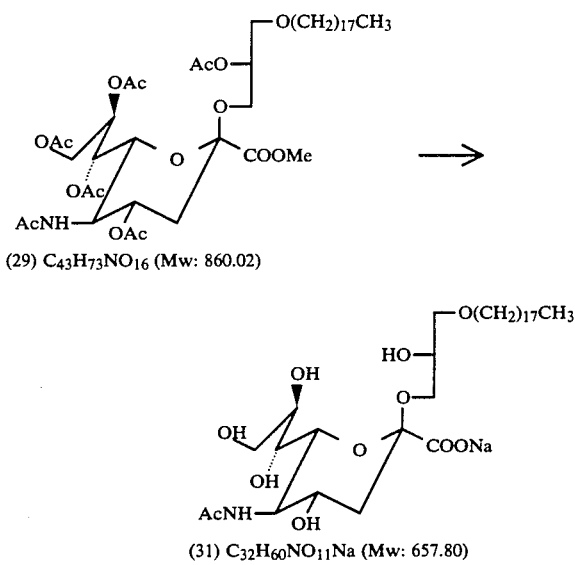

To 147.6 mg (0.17 mmol) of compound (29) there was added 1.02 ml of 1N NaOH solution and the solution was stirred at room temperature for 8 hours. The reaction solution was neutralized with a cation exchange resin (Amberlite IRC-50; pH =7) followed by filtering off the resin, washing the resin with distilled water, purifying the combined filtrate and washing by column chromatography (ODS 60Å, YAMAMURA CHEMICAL LABORATORIES; 60/200 mesh, solvent=water, methanol), collecting the methanol fractions, distilling the solvent therefrom and lyophilizing the resultant residue to obtain compound (31) (90 mg) as white powder. The yield was 79.5%.

Physical Properties of Compound (31)
$^1$H NMR (500 MHz, C$_5$D$_5$N, TMS): δH 0.892 (s, —CH$_3$), 2.010 (s, —NHCOCH$_3$), 2.400 (t, H-3ax) and 3.079 (q, H-3eq).

As discussed above in detail, it is confirmed that according to the method of the present invention, novel sialocylglycerolipids as sodium salts of sialic acid-containing lipid derivatives were synthesized.

It is also proved that the method of the present invention makes it possible to simplify the steps of preparing sialocylglycerolipids and to enhance the yield thereof.

What is claimed is:

1. A sialocylglycerolipid of the following formula (I):

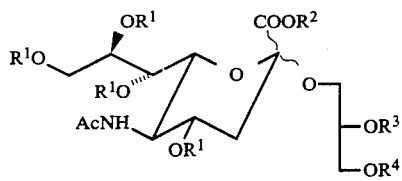

wherein $R^1$ represents a hydrogen atom or a $CH_3CO$—group; $R^2$ represent an alkali metal, a hydrogen atom or a lower alkyl group; $R^3$ represents a hydrogen atom or a $C_nH_{2n+1}$—group; and $R^4$ represent a $C_nH_{2m+1}$-group, wherein each of n and m is an integer ranging from 1 to 13 and 15 to 30.

2. The sialocylglycerolipid of claim 1, wherein $R^2$ is a sodium atom.

3. The sialocylglycerolipid of claim 1, wherein $R^3$ is a hydrogen atom or a $C_nH_{2n+1}$-group wherein n is an integer of 6, 10, 18 or 22.

4. The sialocylglycerolipid of claim 1, wherein $R^4$ is a $C_mH_{2m+1}$-group wherein m is an integer of 6, 10, 18 or 22.

5. The sialocylglycerolipid of claim 1, wherein $R^2$ is a sodium atom, $R^3$ is hydrogen atom or a $C_nH_{2n+1}$-group, and $R^4$ is a $C_mH_{m+1}$-group, wherein each of n and m is an integer of 6, 10, 18 or 22.

6. The sialocylglycerolipid of claim 1, wherein each of n and m is an integer ranging from 1to 10 and 18 to 20.

7. A process for preparing a sialocylglycerolipid of formula (III):

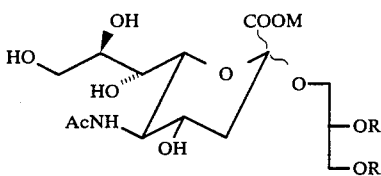

wherein M is an alkali metal, $R^3$ represents a hydrogen atom or a $C_nH_{2n+1}$-group, and $R^4$ represents a $C_mH_{2m+1}$ group, wherein each of n and m is an integer ranging from 1 to 30, comprising:
treating a compound of formula (II):

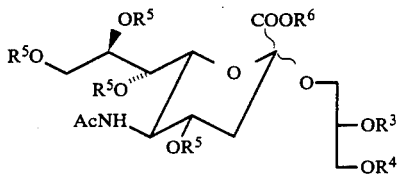

wherein $R^5$ represents a $CH_3CO$—group; $R^6$ a hydrogen atom or a lower alkyl group; and $R^3$ and $R^4$ are the same as defined above, in an aqueous alkaline solvent.

8. The process of claim 7, wherein M is a sodium atom.

9. The process of claim 7, wherein $R^3$ is a hydrogen atom or a $C_nH_{2n+1}$-group, wherein n is an integer of 6, 10, 18 or 22.

10. The process of claim 7, wherein $R^4$ is a $C_mH_{2m+1}$ group, wherein m is an integer of 6, 10, 18 or 22.

11. The process of claim 7, wherein $R^2$ is a sodium atom, $R^3$ is a hydrogen atom or a $C_nH_{2n+1}$-group, and $R^4$ is a $C_mH_{2m+1}$ group, wherein each of m and n is an integer of 6, 10, 18 and 22.

12. The process of claim 7, wherein the treatment is performed in tetrahydrofuran, methanol or ethanol under alkaline conditions.

13. The process of claim 7, wherein each of n and m is an integer ranging from 1 to 10 and 18 to 20.

* * * * *